(12) United States Patent
Rana et al.

(10) Patent No.: US 8,685,472 B2
(45) Date of Patent: Apr. 1, 2014

(54) SKIN WHITENING COMPOSITION CONTAINING CHIA SEED EXTRACT

(75) Inventors: Jatinder Rana, Grand Rapids, MI (US); Ganesh Diwakar, Grand Rapids, MI (US); Jeffrey Scholten, Grand Rapids, MI (US)

(73) Assignee: Access Business Group International LLC, Ada, MI (US)

( * ) Notice: Subject to any disclaimer, the term of this patent is extended or adjusted under 35 U.S.C. 154(b) by 199 days.

(21) Appl. No.: 12/715,156

(22) Filed: Mar. 1, 2010

(65) Prior Publication Data

US 2011/0212201 A1    Sep. 1, 2011

(51) Int. Cl.
*A61K 36/00* (2006.01)
*A61K 36/537* (2006.01)
*A61K 36/18* (2006.01)

(52) U.S. Cl.
CPC ............... *A61K 36/537* (2013.01); *A61K 36/18* (2013.01); *A61K 2236/33* (2013.01)
USPC ............................ 424/769; 424/776; 424/725

(58) Field of Classification Search
CPC .. A61K 36/18; A61K 36/537; A61K 2236/33
See application file for complete search history.

(56) References Cited

U.S. PATENT DOCUMENTS

| | | | |
|---|---|---|---|
| 4,684,522 A | 8/1987 | Marissal et al. | 424/195.1 |
| 4,942,033 A | 7/1990 | Aubert et al. | 424/195.1 |
| 4,948,583 A | 8/1990 | Grollier et al. | 424/195.1 |
| 5,059,426 A | 10/1991 | Chiang et al. | 424/449 |
| 5,229,130 A | 7/1993 | Sharma et al. | 424/449 |
| 5,348,943 A * | 9/1994 | Pickart | 514/18.6 |
| 5,716,605 A | 2/1998 | Onitsuka et al. | 424/70.1 |
| 5,716,800 A | 2/1998 | Meybeck et al. | 435/52 |
| 5,747,006 A | 5/1998 | Dornoff et al. | 424/62 |
| 5,980,904 A | 11/1999 | Leverett et al. | 424/195.1 |
| 6,086,861 A | 7/2000 | Onitsuka et al. | 424/70.1 |
| 6,348,204 B1 | 2/2002 | Touzan | 424/401 |
| 6,403,125 B1 | 6/2002 | Pauly et al. | 424/769 |
| 6,410,048 B1 | 6/2002 | Fotinos | 424/447 |
| 6,461,648 B2 | 10/2002 | Soulier et al. | 424/777 |
| 6,551,625 B1 | 4/2003 | Hilaire et al. | 424/725 |
| 6,761,913 B2 | 7/2004 | Butters et al. | 424/758 |
| 6,800,292 B1 | 10/2004 | Murad | 424/401 |
| 6,994,874 B2 | 2/2006 | Leverett et al. | 424/725 |
| 7,060,304 B2 | 6/2006 | Leverett et al. | 424/725 |
| 7,060,693 B1 | 6/2006 | Dumas et al. | 514/170 |
| 7,128,914 B2 | 10/2006 | Leclerc et al. | 424/195.17 |
| 7,192,616 B2 | 3/2007 | Cals-Grierson et al. | 424/769 |
| 7,247,321 B2 | 7/2007 | Leverett et al. | 424/725 |
| 7,364,759 B2 | 4/2008 | Leverett et al. | 424/725 |
| 7,381,436 B2 | 6/2008 | Andre et al. | 424/756 |
| 7,402,669 B2 | 7/2008 | Loiseau et al. | 536/128 |
| 7,638,640 B2 | 12/2009 | Seeram et al. | 549/278 |
| 7,722,904 B2 | 5/2010 | Schneider et al. | 424/746 |
| 2002/0168431 A1 | 11/2002 | Belna | 424/746 |
| 2002/0192178 A1 | 12/2002 | Pelletier et al. | 424/70.14 |
| 2004/0208838 A1 | 10/2004 | Leverett et al. | 424/62 |
| 2004/0208839 A1 | 10/2004 | Leverett et al. | 424/62 |
| 2004/0213744 A1 | 10/2004 | Lulla et al. | |
| 2006/0099280 A1 | 5/2006 | Shibuya et al. | 424/756 |
| 2007/0166251 A1 * | 7/2007 | Dayan et al. | 424/62 |
| 2008/0025930 A1 | 1/2008 | Corstjens et al. | 424/59 |
| 2008/0261291 A1 | 10/2008 | De La Llata Romero | 435/267 |
| 2008/0305190 A1 | 12/2008 | Vuksan | 424/746 |
| 2008/0317836 A1 * | 12/2008 | Dorogi et al. | 424/450 |
| 2008/0317933 A1 | 12/2008 | Williamson | 426/629 |
| 2009/0047310 A1 | 2/2009 | Meybeck | 424/401 |
| 2009/0181127 A1 | 7/2009 | Minatelli et al. | 426/63 |
| 2009/0232785 A1 | 9/2009 | Breton et al. | 424/93.44 |
| 2009/0274749 A1 | 11/2009 | Johnson | 424/450 |

FOREIGN PATENT DOCUMENTS

| | | | | |
|---|---|---|---|---|
| EP | 1140002 B1 | 5/2006 | | |
| EP | 1 842 530 A1 | 10/2007 | | |
| FR | 2 773 323 B1 | 2/2000 | | |
| KR | 10-2008-0111249 | 12/2008 | | |
| KR | 2008111249 A | * 12/2008 | | A61K 8/97 |
| WO | WO 02/45680 A1 | 6/2002 | | |
| WO | WO 03/041636 A2 | 5/2003 | | |
| WO | WO 2008/044908 A2 | 4/2008 | | |
| WO | WO 2009/126798 A1 | 10/2009 | | |
| WO | WO 2010/104301 A2 | 9/2010 | | |

OTHER PUBLICATIONS

Pancheco-Palencia et al. Protective Effects of Standardized Pomegranate (*Punica granatum* L.) Polyphenolic Extract in Ultraviolet-Irradiated Human Skin Fibroblasts. Journal of Agricultural Food Chemistry. (2008), 56. pp. 8434-8441.*
Smolinske. Handbook of Food, Drug and Cosmetic Excipients. CRC Press. 1992. p. 307.*
The Herbal Encyclopedia. Retrieved from the internet. Retrieved on Apr. 22, 2011. Web archive date Feb. 10, 2003. <http://classic-web.archive.org/web/20030210135948/http://www.naturalark.com/herbcomb.html>. pp. 1-9.*
Ando, Hideya, et al., "*Linoleic Acid and α-Linolenic Acid Lightens Ultraviolet-Induced Hyperpigmentation of the Skin*", Arch. Dermatol. Res., 290: 1998, pp. 375-381.
Chang, Te-Sheng,"*An Updated Review of Tyrosinase Inhibitors*", Int. J. Mol. Sci. vol. 10, 2009, pp. 2440-2475.
Cho, W., et al., "*Use of Glycan Targeting Antibodies to Identify Cancer-Associated Glycoproteins in Plasma of Breast Cancer Patients*", Anal. Chem.. vol. 80:14, Jul. 15, 2008, pp. 5286-5292. Abstract only. http://www.ncbi.nlm.ni.gov/pubmed/18558770.

(Continued)

*Primary Examiner* — Chris R Tate
*Assistant Examiner* — Russell Fiebig
(74) *Attorney, Agent, or Firm* — Brinks Gilson & Lione; G. Peter Nichols

(57) ABSTRACT

A topical composition includes an alcohol-extracted *Salvia hispanica* seed extract in a glycol carrier in an amount effective for inhibiting melanin content in an individual. The extract may be extracted in a C1-C4 ethanol and resuspended in a glycol carrier with one or more permeation enhancers. The topical composition may further include a *Punica granatum* extract. Methods for making and using the composition for whitening skin in an individual are also described.

7 Claims, 4 Drawing Sheets

(56) References Cited

OTHER PUBLICATIONS

Khan, Mahmud Tareq Hassan, "*Molecular Design of Tyrosinase Inhibitors: A Critical Review of Promising Novel Inhibitors From Synthetic Origins*", Pure Appl. Chem. vol. 79, No. 12, 2007, pp. 2277-2295.

Barry, B. "Properties That Influence Percutaneous Absorption", *Dermatological Formulations*, Marcel Dekker, Inc., New York and Basel, Jan. 1, 1983, pp. 160-172.

Kumar, P. et al., "Selection of Optimum Process, Solvent and Drying Method for Extraction of Antioxidants", *Jurnal Teknologi*, vol. 48, No. F, Jun. 2008, pp. 85-98.

Torti, S. et al., "Extraction of Phenolic Compounds From Fresh Leaves: A Comparison of Methods", *Journal of Chemical Ecology*, Plenum Publishing Corporation, US, vol. 21, No. 2, Jan. 1, 1995, pp. 117-125.

Vinatoru, M. et al., "The Use of Ultrasound for the Extraction, of Bioactive Principles from Plant Materials", *Ultrasonics: Sonochemistry*, Butterworth-Heineman, GB, vol. 4, No. 2, Apr. 1, 1997, pp. 135-139.

International Search Report and Written Opinion for PCT/US2011/023671, dated Oct. 4, 2010, 15 pages.

\* cited by examiner

SKIN WHITENING COMPOSITION CONTAINING CHIA SEED EXTRACT

This invention relates generally to skin whitening or skin lightening compositions for cosmetic use.

The present invention relates to a skin-whitening (or skin-lightening) composition for external use containing an alcohol-extracted chia (*Salvia hispanica*) seed extract and to a method of whitening skin by topically applying a composition containing an effective amount the alcohol-extracted *Salvia hispanica* seed extract.

Skin color is primarily determined by the amount of melanin present in the skin. Melanin is a brown-black pigment present in the skin, which protects the body from the damaging effects of ultraviolet radiation. Due to the dark color of the pigment, lower amounts of melanin result in lighter skin color while higher amounts result in darker skin color. Melanin is formed by the oxidation of the amino acid tyrosine to dihydroxyphenalanine in melanocytes via a process termed melanogenesis. Within melanocytes, melanin is bound to a protein matrix to form melanosomes, where tyrosinase converts tyrosine to eumelanin (black pigment) or pheomelanin (yellowish and reddish pigment). Melanin biosynthesis involves a chain of oxidative reactions catalyzed by series of enzymes. In addition to tyrosinase, DOPAchrome tautomerase (TRP-2) and DHICA oxidase (TRP-1) are responsible for converting DOPAchrome to 5,6-dihydroxyindole-2-carboxy acid, which leads to the formation of eumelanin.

In some cases, it is desirable to reduce or inhibit melanogenesis, for example, to cause skin whitening or lightening, to eliminate "age spots", lentigenes, or to reduce hyperactive melanocytes. Thus, in recent years, cosmetic compositions have been developed to reduce the amount of melanin in the skin and therefore, whiten the skin. These development efforts have focused on whitening agents that inhibit the function or activity of tyrosinase or block the chain reaction at various points in the melanogenesis pathway. Thus, compositions including these agents may achieve a skin whitening or lightening effect by blocking tyrosinase activity, reducing tyrosinase synthesis, inhibiting TRP-1 and/or TRP-2, blocking melanin transfer from melanocytes to keratinocytes, and/or accelerating the desquamation of the keratinocytes. Accordingly, whitening compositions have been developed that include hydroquinone, phenylthiourea, vitamin C and its derivatives, kojic acid, arbutin, various polyphenols, including flavonoids, such as flavones, flavonols, flavanoids, flavanols, isoflavonoids, chalcones, and catechin; linoleic acid, α-linolenic acid, glutathione, cysteine, endothelin antagonists, keratinocyte receptor inhibitors, placenta extract, and mulberry extract among others.

Despite the efficacy of the above compounds in producing whiter skin, alternatives that are effective and possess desirable attributes are continually being sought. Botanical source materials, including seeds, are known to carry or store a rich variety of nutritionally or medicinally beneficial bioactive agents, including antioxidants, fatty acids, vitamins, flavonoids, and other phytochemicals. In many cases, these bioactive agents include known whitening agents present in seed oil preparations. For example, conventional chia (*Salvia hispanica*) seed oil preparations are known to contain high levels of α-linolenic acid and linoleic acid, two fatty acids known to suppress melanin production (Ando et al., Arch. Dermatol. Res., 290:375-381, 1998). Fatty acids, such as α-linolenic acid and linoleic acid may be extracted from plant seed materials as oils produced by a number of different methods. These include expeller pressing methods employing mechanical pressure and friction, or may involve the use of chemical solvents, such as hexane or alcohol, in conjunction with various temperature, pressure, or distillation steps. A given extraction process may cause physical and chemical changes to the bioactive agents resulting in different biochemical profiles, however.

The inventors of the present application have unexpectedly found that an alcohol-extracted *Salvia hispanica* seed extract according to the present invention provides a dramatically increased efficacy in reducing total melanin content compared to compositions containing otherwise identical amounts of linoleic acid and/or α-linolenic acid alone.

SUMMARY

It is an object of the present invention to provide a topical composition that includes a glycol carrier and an alcohol-extracted *Salvia hispanica* seed extract in an amount effective for inhibiting melanin content in an individual. The seed extract may be prepared by extracting *Salvia hispanica* seeds in a C1-C4 ethanol and resuspending the resultant dried extract in a glycol carrier, such as pentylene glycol. The composition may further include a permeation enhancer, such as dimethyl sulfoxide (DMSO). In addition, the composition may further include a *Punica granatum* (Pomegranate) extract. The composition may be provided in a form that is suitable for spreading on the skin of a subject such as by hand application.

The present invention further provides a method for making the above topical compositions for use in a method for whitening skin in an individual.

DETAILED DESCRIPTION

Figure 1:
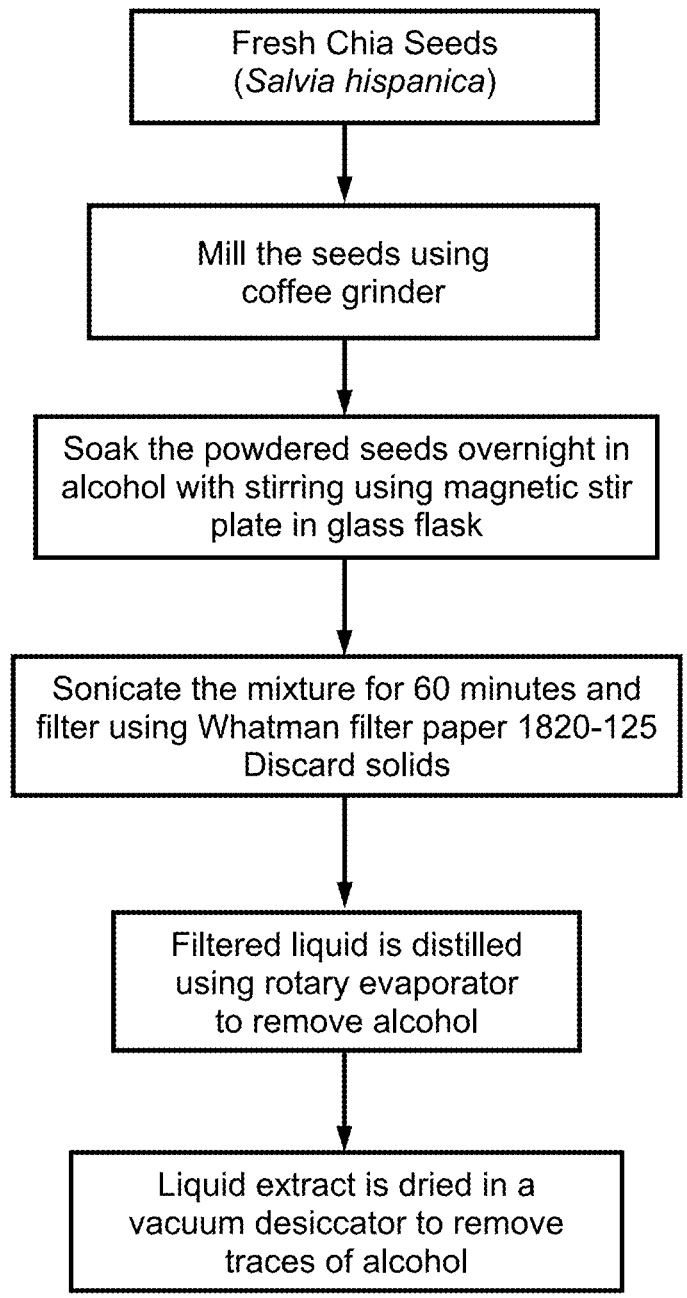
FIG. 1 is a flow chart depicting an exemplary alcoholic extraction process.

In order to provide a clear and consistent understanding of the specification and claims, the following definitions are provided.

The terms "skin whitening", "whitening skin", or "skin lightening" refer to one or more effect(s) of suppressing melanin production or melanin content in an individual, including prevention or inhibition of pigmentation, lightening of dark skin, lightening or removal of hyperpigmentations, especially local hyperpigmentations and defective pigmentations; prevention and/or improvement of skin dullness, skin darkening by sunburn, spots, and freckles.

The term "glycol" as used herein refers to an organic compound having two hydroxyl (OH) groups attached to different carbon atoms.

The term "carrier" refers to a composition maintaining one or more plant and/or seed extract(s) in a soluble and homogenous state in a material form suitable for topical delivery, which is nontoxic and which does not interact with other components in the carrier in a deleterious manner.

The term "permeation enhancer" refers to a compound useful for increasing the permeability of a cosmetically active agent through skin, i.e., so as to increase the rate at which the active agent permeates through the skin.

Unless indicated otherwise, all proportions and percentages cited in this disclosure are by weight. Further, the contents of all references, patents, and published applications cited throughout this patent are hereby incorporated by reference herein.

In one embodiment, the present invention provides a topical composition including a glycol carrier and an alcohol-extracted *Salvia hispanica* (chia) seed extract in an amount effective for inhibiting melanin content in an individual. The compositions (or formulations) of the present invention are particularly suited for topical application as skin whitening (or skin lightening) agents.

*Salvia hispanica* seed oil preparations are known to contain α-linolenic acid and linoleic acid, two fatty acids with known melanin-suppressing activities. Initial attempts to evaluate the efficacy of a *Salvia hispanica* seed oil extract in a melanin inhibition assay were unsuccessful due to poor solubility and poor cell permeation of the seed oil components with or without surfactants or cell permeation enhancers, such as DMSO. Specifically, there was no observed effect on melanin content in a murine melanocyte cell line (i.e., melan-a) treated with *Salvia hispanica* seed oil samples alone or in the presence of DMSO.

As a follow-up to these experiments, an alcohol-extracted *Salvia hispanica* seed extract was prepared and incorporated in a pentylene glycol: DMSO carrier (see FIG. 1, for example). When tested for efficacy in a melanin inhibition assay, a topical composition containing this alcohol-extracted *Salvia hispanica* seed extract was found to exhibit a dramatically increased efficacy in reducing total melanin content in melan-a cells compared to a conventional *Salvia hispanica* seed oil preparation and compared to the levels of linoleic acid and/or α-linolenic acid present in the alcohol-extracted *Salvia hispanica* seed extract (see FIGS. 2 and 3). It is believed that an alcohol-extracted *Salvia hispanica* seed extract according to the present invention contains other melanin-reducing substances apart from linoleic acid and/or α-linolenic acid which are primarily responsible for the dramatically increased efficacy in reducing total melanin content.

Figure 4:
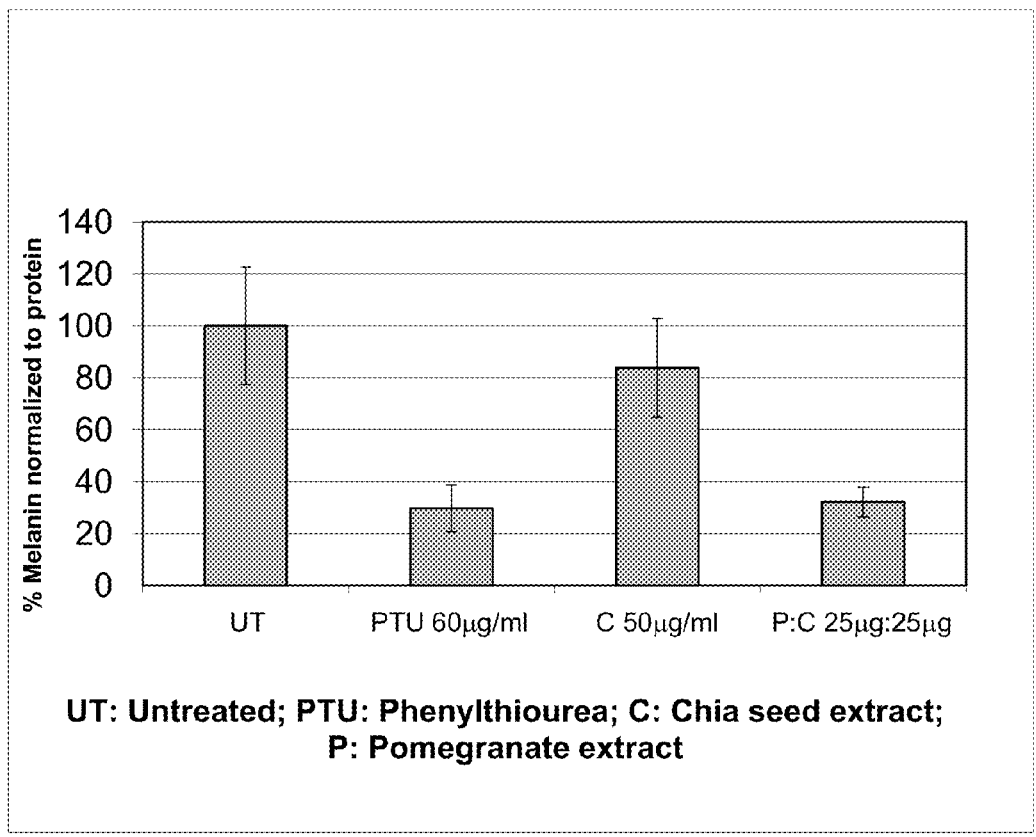
FIG. 4 illustrates the results of a melanin inhibition assay evaluating treatment of melan-a cells with an alcohol-extracted *Salvia hispanica* seed extract in combination with a *Punica granatum* (pomegranate) extract.

Applicants have surprisingly discovered that treatment of melan-a cells with an alcohol-extracted *Salvia hispanica* seed extract at 25 μg/ml in combination with a pomegranate extract at 25 μg/ml reduced total melanin content to a significantly higher degree (i.e., 68% reduction) than using an alcohol-extracted *Salvia hispanica* seed extract alone at 50 μg/ml (i.e., 16% reduction; see FIG. 4).

In accordance with the present invention, *Salvia hispanica* seeds may be prepared for extraction by grinding or pressing the seeds into a powdered material in a known manner as by mechanical disruption in a blender, coffee grinder or other similar means. The powdered material may be exposed to one or more solvents, including at least one alcohol, for a sufficient time to facilitate extraction of *Salvia hispanica* components. In one embodiment, the extract is obtained by exposing a *Salvia hispanica* seed extract to a single alcoholic solvent.

Exemplary alcoholic solvents include but are not limited to C1-C4 alcohols, such as methanol, ethanol, propanol, isopropanol, and butanol; hydro-alcohols or mixtures of alcohol and water, including hydroethanol; polyhydric alcohols such as propylene glycol and butylene glycol; and fatty alcohols. Any of these alcoholic solvents may be used in the form of a mixture. In one embodiment, the seed extract is extracted using 95% ethanol.

The powdered seed extract may be exposed to a single alcoholic solvent or it may be sequentially exposed to a plurality of solvents, including at least one alcohol. When using a plurality of solvents, the alcohol-extracted extract may be prepared by exposing the powdered seed material to a first solvent, removing the residue, and exposing the residue to a second solvent. This process may be repeated a number of times using any number of different solvents varying in solvent strength. The number of extraction steps included may depend on various factors, including the melanin inhibiting ability of the various fractions obtained at each step. Any recovered residue may be dried and suspended in a suitable carrier and used separately or may be combined with one or more of the other fractions, based on the melanin inhibiting ability of the recovered fractions.

Particulate residue may be separated from the extracted components in the solvent by filtration or other separation means known to those of skill in the art. The extracted components may be sonicated prior to filtration to further enhance the extraction of the component substances.

A filtered liquid containing the extracted seed component substances may be distilled using a rotary evaporator or other similar means to remove most of the solvent. A vacuum desiccator or other other similar means may be utilized to remove any further traces of the solvent to form a dried extract. The dried extract may be resuspended in a cosmetically acceptable carrier. A suitable carrier will maintain the extract in a soluble and homogenous state in a material form suitable for topical delivery, which is nontoxic and which does not interact with other components in the carrier in a deleterious manner. In one form, the carrier is suitable for spreading on the skin of a subject such as by hand application. The dried extract may be suspended in the carrier at a concentration between about 0.1 mg/ml and about 500 mg/ml, between about 1 mg/ml and about 250 mg/ml, or between about 20 mg/ml and about 150 mg/ml.

The alcohol-extracted *Salvia hispanica* seed extract may be suspended in a glycol carrier. Exemplary glycols include but are not limited to aliphatic diols, such as 1,2-ethanediol (ethylene glycol), 1,2-propandiol (propylene glycol), 2-methyl-1,3-propanediol, 1,3-butanediol (butylene glycol), 2,3-butanediol (2,3-butylene glycol), 1,3-pentanediol (pentylene glycol), 1,2-hexanediol, 1,6-hexanediol, 2-methyl-2,4-pentanediol (hexylene glycol), 1,2-octanediol (caprylyl glycol), and 1,2-decanediol (decylene glycol). In some embodiments, more than one glycol may be present. In other embodiments, other solvents (or "co-solvents"), particularly non-volatile solvents, may be present in the composition, including but not limited to esters and other polyols such as glycerin, polyethylene glycols, polypropylene glycols, and mixtures thereof. The glycol carrier may be present in a composition containing the alcohol-extracted *Salvia hispanica* seed extract at a final concentration between about 0.01% and about 2%, or between about 0.05% and about 0.5%.

In an embodiment, the alcohol-extracted *Salvia hispanica* seed extract is suspended in pentylene glycol. Pentylene glycol is both water and oil-soluble and is a humectant and moisturizing agent with antimicrobial activity, including an ability to synergistically increase the antimicrobial activity of parabens.

More broadly, *Salvia hispanica* seed extracts, plant extracts, and/or other active agents may be included, either individually or collectively, in a variety of alternative cosmetically acceptable carriers. A suitable carrier will maintain the extract in a soluble and homogenous state in a material form suitable for topical delivery, which is nontoxic and which does not interact with other components in the carrier in a deleterious manner. Examples of cosmetically acceptable carriers suitable for the embodiments of the present invention include, but are not limited to, water, glycols, polyols, C1-C4 alcohols, fatty alcohols, fatty ethers, fatty esters, glycerin, vegetable oils, mineral oils, lecithin, hydrogenated lecithin, liposomes, laminar lipid materials, phospholipids, polyglycols, or combinations thereof.

In a further aspect, the present invention provides a topical composition including an alcohol-extracted *Salvia hispanica* seed extract in a glycol carrier along with a *Punica granatum* (pomegranate) extract in combined amounts effective for inhibiting melanin content in an individual. Applicants have surprisingly discovered an enhanced efficacy in reducing total melanin content when applying a composition containing an alcohol-extracted *Salvia hispanica* seed extract in combination with a pomegranate extract as further described below.

The pomegranate extract may be derived from pomegranate fruit, husk, arils, seed, bark, leaves, or combinations thereof. In an embodiment, a pomegranate fruit extract and/or husk extract in powdered form is employed in the topical compositions of the present invention. The pomegranate extract may be obtained commercially or it may be obtained using any of the extraction techniques discussed herein or known to those skilled in the art. Suitable commercial sources for pomegranate extract include Nature's Way (Springville, Utah), Nature's Herbs (American Fork, Utah), Swansen's Health Products (Fargo, N. Dak.) and Doctor's Trust Vitamins (Orlando, Fla.).

Pomegranate extracts are an abundant source of antioxidants, particularly polyphenols, especially ellagitannins. Ellagitannins consist of polymers of glucose and ellagic acid, gallic acid and/or hexahydroxydiphenic acids. Punicalagins are the most abundant ellagitannins in pomegranate extracts. Other ellagitannins include the punicalagin isomer, 2,3-hexahydroxydiphenoyl-4,6-gallagylglucose, punicalin (4,6-gallagylglucose), gallagic acid, ellagic acid, and various glycosides thereof (ellagic acid hexoside, pentoside, rhamnoside etc.). The pomegranate extract may contain a punicalagin content of at least about 5%, at least about 10%, at least about 20%, at least about 30%, or higher; or between about 5% and about 40% or between about 10% and about 30%.

A topical composition according to the present invention may also include additional skin whitening or skin lightening agents known to reduce total melanin content in skin. Exemplary skin whitening or skin lightening agents include but are not limited to, bearberry extract and its derivatives; acerola cherry fermentate and its derivatives; black cohosh extract and its derivatives; asparagus extract and its derivatives; polyphenols; including flavonoids; such as flavones; flavonols, flavanoids, flavanols, isoflavonoids, chalcones, and catechin; orange extract and its derivatives; rosemary extract and its derivatives; lemon extract and its derivatives; cucumber extract and its derivatives; mulberry extract and its derivatives; placenta extract and its derivatives; licorice extract and its derivatives; gingko extract, carob extract, rose fruit extract, geranium herb extract, clove extract, alfalfa extract, cinnamon extract, and sweet marjoram extract; extracts from *Arnica, Perilla*, cola ed Caballo, Piri-Piri, Pinon Negro, Pinon Blanco, Concha blanca, *Baliospermum montanum, Melia azadirachta, Convolvulus arvensis*, Gaiyo, Sansonin, Syuroyo, Seimkko, Soukyo, Taiso, Hakusempi, *Woodfordia fructosa, Lagerstroemia speciosa*, passiflorine, tepezcohite, amoule, Hobiyu, Baffalo Uri, Achote, Guayule, Adhatoda, *Cymbopogon nardus, Desmodium gangeticum, Murraya koenigii, Smilax zeylanica, Gastrodia elata*, Karukeija, *Biota orientalis*, Kichiascoporia, Arecatachu, *Phyllostachys nigra* leaves, *Atractylodes japonica*, Koidzumi, Tila, Camotede azafran, Jamaica, Poleo verde, Navo negro, *Cyperus*, Kanzo, *Broussonetia*, Karojitsu, Trichosanthis radix, Dioscorea phizoma, and Aquilliaria; kojic acid and its derivatives; arbutin and its derivatives; teprenone, dihydroxy-isoquinoline, indomethacin, 3-hydroxymanule, vitamin C and its precursors and derivatives, including ascorbic acid, tetrahexyldecyl ascorbate, ascorbyl palmitate; hydroquinone and its derivatives; linoleic acid, α-linolenic acid, glutathione, cysteine and its derivatives vitamin K and its precursors and derivatives, (including vitamin K1-K7), thiazolidinone derivatives, kynurenine and its derivatives and salts; endothelin antagonists, keratinocyte receptor inhibitors, including mixtures or combinations of any of the whitening agents described herein.

Additional cosmetically useful plant extracts or ingredients include *Avena sativa* (oat) kernel extract, evening primrose seed extract, L-ergothioneine, hydrolyzed soy protein, yeast extract, *Lentinus enodes* extract, *Nymphaea alba* flower extract, and *Perilla frutescens* leaf extract; as well as plant extracts or ingredients from *Centella, Echinacea, Alpinia*, and *Rosmarinus officinalis*.

The amount of extract present in a skin whitening composition will depend upon several factors, including the desired level of melanin inhibition, the melanin inhibiting level in a particular extract or composition, and other factors. The extract may comprise between about 0.01 and about 20% (wt/wt) of the total composition. The extract may comprise between about 0.05 and about 10% (wt/wt) of the total composition. The extract may comprise between about 0.1 and 5% (wt/wt) of the total composition.

Additional extracts or ingredients for use in the topical composition of the present invention are described in U.S. Pat. No. 5,747,006 to Dornoff et al. and U.S. Pat. Nos. 5,980, 904, 6,994,874, 7,060,304, 7,247,321, and 7,364,759 to Leverett et al., the disclosures of which are expressly incorporated by reference herein.

A topical composition according to the present invention may also include one or more permeation enhancer(s) for increasing the permeability of skin to one or more cosmetically active agents so as to increase the rate at which the active agent(s) permeate through the skin. Exemplary permeation enhancers include, but are not limited to, dimethylsulfoxide (DMSO), dimethyl formamide (DMF), N,N-dimethylacetamide (DMA), decylmethylsulfoxide ($C_{10}$MSO), polyethylene glycol monolaurate (PEGML), glycerol monolaurate, lecithin, 1-substituted azacycloheptan-2-ones, particularly 1-n-dodecylcyclazacycloheptan-2-one (available under the trademark Azone® from Nelson Research & Development Co., Irvine, Calif.), alcohols, and the like. Additional permeation enhancers include those described in U.S. Pat. No. 5,059,426 to Chiang et al. and U.S. Pat. No. 5,229,130 to Sharma et al., the disclosures of which are incorporated by reference herein. The permeation enhancer may be present in a topical composition of the present invention at a concentration between about 0.005% to about 0.5%, or between about 0.1 and about 0.02%. In addition, the ratio between the glycol carrier and the permeation enhancer may range between about 10:1 to about 1:1, or between about 5:1 to about 2:1.

Other cosmetic ingredients may be incorporated in a given topical composition. Other cosmetic ingredients may include additional plant extracts, vitamins, minerals, anti-oxidants, collagen stimulating agents, skin conditioning agent(s), such as humectants and emollients; alcohols, fats and oils, surfactants, fatty acids, silicone oils, thickeners, viscosity modifiers, emulsifiers, stabilizers, surfactants, coloring agents, anesthetics, anti-allergenics, anti-irritants, anti-fungals, antimicrobials, anti-inflammatory agents, antiseptics, chelating agents, film formers, fragrances, insect repellents, lubricants, pharmaceutical agents, photostabilizing agents, preservatives, skin protectants, sunscreens, or any combinations thereof.

Cosmetically useful vitamins, minerals and/or anti-oxidants for topical application may include vitamin A and its precursors or derivatives (e.g., beta-carotene, retinyl palmitate); vitamin B3 and its precursors or derivatives (e.g., niacinamide); vitamin B5 and its precursors or derivatives (e.g. panthenol and its precursors, derivatives, or equivalents as described in CTFA Cosmetic Ingredient Handbook, The Cosmetic, Toiletry and Fragrance Association. Inc., pp. 272-273, 1992); vitamin C and its precursors or derivatives (e.g., tetrahexyldecyl ascorbate, ascorbyl palmitate); vitamin E and its precursors or derivatives (e.g., d-alpha-tocopherol, tocopheryl acetate); vitamin K and its precursors or derivatives; selenium and its derivatives (e.g., L-selenomethionine); and alpha lipoic acid.

Humectants include polyhydric alcohols for moisturizing, reducing scaling and stimulating removal of built-up scale from the skin. Typical polyhydric alcohols include polyalkylene glycols, alkylene polyols and their derivatives. Illustrative are propylene glycol, dipropylene glycol, polypropylene glycol, polyethylene glycol, sorbitol, hydroxypropyl sorbitol, hexylene glycol, 1,3-butylene glycol, 1,2,6-hexanetriol, ethoxylated glycerin, propoxylated glycerin and mixtures thereof.

When the conditioning agent is an emollient it may be selected from hydrocarbons, fatty acids, fatty alcohols and esters. Exemplary hydrocarbon type emollients include petrolatum, mineral oil, polyolefins such as polydecene, and paraffins such as isohexadecane (e.g. Permethyl 99® and Permethyl 101®). Exemplary non-limiting skin conditioning agents, humectants, emollients, emulsifiers, viscosity modifiers, and preservatives include those listed in Table 1 below.

The compositions of the present invention may be formulated in any convenient form suitable for topical application to the skin. Such product forms include, but are not limited to, aerosol spray, cream, dispersion, emulsion, foam, gel, liquid, lotion, mousse, ointment, pomade, powder, pump spray, solid, solution, stick, and towelette. A suitable formulation will provide the composition in a form such that it can be applied to the skin of a subject and spread on the skin such as be the hand of the subject. For example, an amount of the composition sufficient to cover from about 1 mm to about 20 mm, or from about 5 mm to about 10 mm will be suitable to be spread by hand in the area of interest. Of course it will be appreciated that the application can encompass multiple locations.

In some embodiments, plant extracts, including the alcohol-extracted *Salvia hispanica* seed extract and the pomegranate extract may be encapsulated in liposomes or configured as a liposomal formulation. Liposomes may be used as delivery agents to facilitate transfer of any of the above described plant extracts or other cosmetically active agents into the dermis of skin. For example, a liposome or liposomal formulation may contain lecithin and water. The liposomes may include conventional phospholipids, oleic acid and/or cholesterol hemisuccinate from vegetable-derived sources, e.g., soybean or they may be produced from other suitable sources conventionally known to those skilled in the art. Exemplary liposome formulations are described in pending U.S. application Ser. No. 12/245,528, filed Oct. 3, 2008, entitled "Composition and Method for Preparing Stable Unilamellar Liposomal Suspension", the disclosures of which are expressly incorporated by reference herein. Other delivery agents may be used for dermal delivery in place of the liposomes, including, but not limited to skin delivery vehicles known to those skilled in the art, including emulsions, microemulsions, nanoemulsions, nanoparticles, microspheres, ethosomes, transfersomes, and niosomes.

In another embodiment, the carrier may be in the form of a homogeneous phase formulation or in the form of an emulsion or microemulsion including, but not limited to, oil-in-water, water-in-oil and multiple including triple, phase emulsions. These emulsions can cover a broad range of consistencies including thin lotions (which can also be suitable for spray or aerosol delivery), creamy lotions, light creams and heavy creams. Other suitable topical carriers include anhydrous liquid solvents such as oil and alcohol; aqueous-based single phase liquid solvent (e.g., hydro-alcoholic solvent system); anhydrous solid and semisolid (such as gel and stick); and aqueous based gel and mousse system.

The present invention also provides a method for preparing an alcohol-extracted *Salvia hispanica* seed extract, including the following steps: (a) providing a source of *Salvia hispanica* seeds; (b) milling or grinding the seeds into a powdered seed form; (c) adding an alcoholic solvent to the powdered seed form to form an alcoholic mixture; (d) sonicating the mixture; filtering away the alcoholic solvent from residue remaining in the mixture, resulting in a liquid extract; (e) vacuum drying the liquid extract to form a dried extract; and (f) suspending the dried extract in a glycol to form an alcohol-extracted *Salvia hispanica* extract in an amount effective for inhibiting melanin content in an individual. This method may be modified so as to conform the resulting topical composition to any of those described herein.

The present invention also provides a method of whitening skin (or inhibiting melanin content in skin), whereby an alcohol-extracted *Salvia hispanica* seed extract is topically applied to the skin of an individual. This method may employ any of the topical compositions described herein. In one embodiment, the composition is applied by spreading onto the skin of a subject by hand application. The frequency of topical applications may depend on several factors, including the desired level of melanin inhibition. A composition of the present invention can desirably be applied to the skin once daily or twice daily, such as once in the morning and once in the evening. The amount of the composition used in each application will also depend on several factors, including the desired level of melanin inhibition and the content of the extract melanin-inhibiting substances in the composition.

EXAMPLES

Example 1

Alcohol Extraction of Chia Seeds

FIG. 1 depicts a flow chart of an exemplary alcoholic extraction process. Briefly, fresh *Salvia hispanica* (chia) seeds were milled using a coffee grinder to form a powdered seed extract. The powdered seed extract was soaked in alcohol overnight with stirring using a magnetic stir plate in a glass flask. The seed to alcohol ratio was approximately 1 part powdered seeds to 10 parts alcohol. After 12 hours, the mixture was sonicated for 60 minutes and then filtered using Whatman filter paper (1820-125). The remaining residue was discarded and the filtrate was distilled using a rotary evaporator to remove the alcohol. The resulting liquid extract was vacuum dried in a vacuum desiccator to remove all traces of alcohol so as to form a dried alcohol-extracted *Salvia hispanica* extract. The dried extract was resuspended in a pentylene glycol/DMSO mix for further evaluation in the melanin inhibition assay described below.

Example 2

Melanin Inhibition Assay

Melan-a murine melanocytes (Wellcome Trust Functional Genomics Cell Bank, St. George Hospital, London, UK) were plated one day prior to treatment in 24 well plates at a density of $5 \times 10^4$ cells per well in 1 ml of melan-a cell medium (RPMI-1640, 10% Fetal Bovine Serum (FBS), 1% Penicillin/Streptomycin, 100 µM β-mercaptoethanol, 2 mM L-Glutamine and 200 nM Phorbol 12-myristate 13-acetate) in a 10% $CO_2$ incubator maintained at 37° C. After seeding the cells for 24 hours in triplicate, cells were treated as indicated below. After two days of treatment, the culture media was changed and fresh samples were added and incubated overnight. The cells were initially tested for cell viability and cytotoxicity using the WST-1 assay (Roche Applied Science). Following the WST-1 assay, the cells were washed in 1×PBS and harvested in extraction buffer for melanin isolation and quantification.

Cells from each well of the 24 well plate were harvested in cell lysis buffer (1% Triton X 100, 50 mM Tris, 2 mM EDTA, 150 mM NaCl, pH 7.5 supplemented with a complete protease inhibitor cocktail). Cell lysates were centrifuged at 20,000 g for 10 min at 4° C. Protein levels in the supernatant were quantified using a Pierce BCA Protein assay kit (Thermo Scientific Corp). Melanin-containing precipitates were washed in 100 µl of ethanol:ether (1:1) for 10 min at room temperature. The ethanol:ether solution was discarded and the melanin-pellets were dissolved in 200 µl of 2N NaOH in 20% DMSO solution and incubated at 70° C. for 60 min. The resulting melanin extract was analyzed by measuring absorbance at 490 nm. The melanin content in each sample was evaluated by normalizing each sample to the total amount of protein.

Example 3

Efficacy of Alcohol-Extracted Chia Seed Extracts

Figure 2:
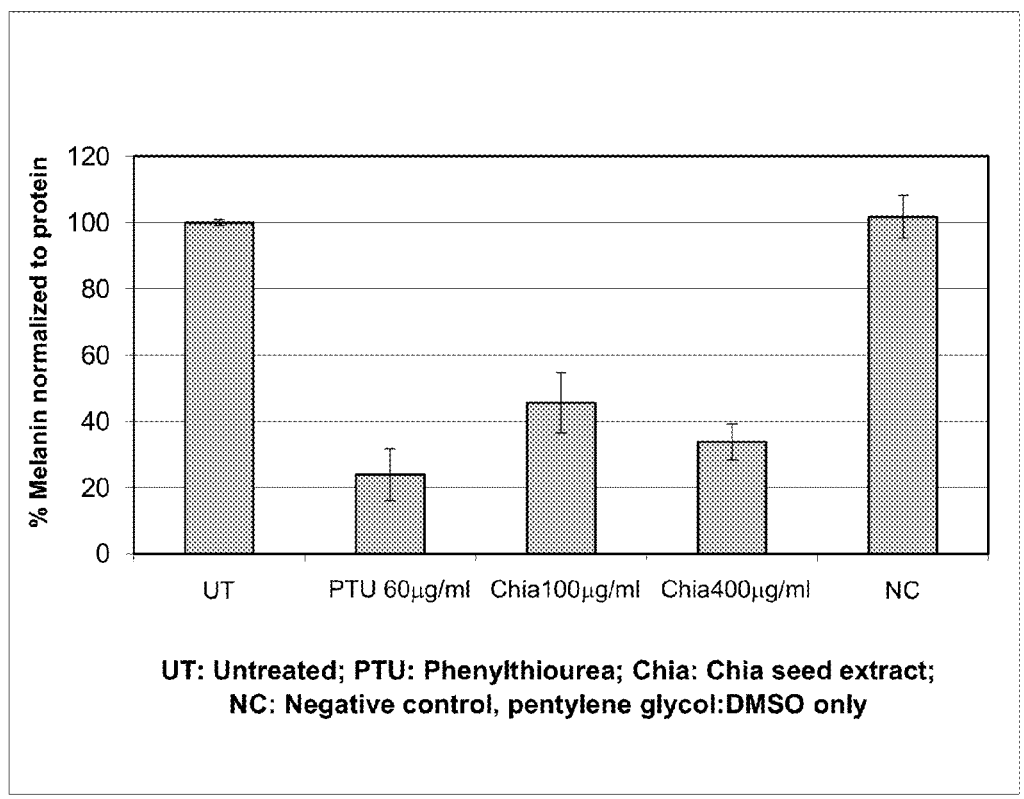
FIG. 2 illustrates the results of a melanin inhibition assay evaluating treatment of melan-a cells with an alcohol-extracted *Salvia hispanica* (chia) seed extract.

Initial attempts to evaluate the efficacy of a *Salvia hispanica* seed oil extract in a melanin inhibition assay were unsuccessful, due to poor solubility and poor cell permeation of the seed oil components with or without surfactants or cell permeation enhancers, such as DMSO (not shown). As a follow-up to these experiments, an alcohol-extracted chia seed extract was prepared in a pentylene glycol: DMSO carrier and tested for efficacy using the melanin inhibition assay described above. Briefly, a dried alcohol-extracted *Salvia hispanica* (chia) seed extract (CSE) was dissolved in a 91% pentylene glycol/0.91% DMSO mix to form a solution containing 106 mg/ml CSE. Melan-a cells were treated as described above with 1 ml culture medium containing CSE at a final concentration of 100 µg/ml or 400 µg/ml in 0.36% pentylene glycol: 0.036% DMSO. Positive control cells were treated with phenylthiourea (PTU) at a final concentration of 60 µg/ml in 1 ml culture medium containing 0.36% pentylene glycol: 0.036% DMSO. Negative control cells were treated with 0.36% pentylene glycol: 0.036% DMSO alone. The results of this experiment are shown in FIG. 2.

In contrast to the chia seed oil extracts, the alcohol-extracted chia seed extracts were found to significantly reduce melanin content in melan-a cells in a dose-dependent manner. Specifically, melanin content was reduced by about 54% at a 100 µg/ml CSE concentration and by about 66% at a 400 µg/ml concentration (FIG. 2). No inhibitory effects were observed in the negative control samples. WST-1 assays showed that the alcohol extracted chia seed extracts were not cytotoxic to melan-a cells at the concentrations tested.

Example 4

Efficacy of Linoleic Acid and α-Linolenic Acid

The relative efficacy of linoleic acid and α-linolenic acid at concentrations in excess of those present in the alcohol-extracted *Salvia hispanica* seed extracts was evaluated in a melanin inhibition assay as described above. Briefly, melan-a cells were separately treated with linoleic acid or α-linolenic acid in 1 ml culture medium at a final concentration of 100 µg/ml in 0.36% pentylene glycol: 0.036% DMSO. The 100 µg/ml linoleic acid concentration was about 22-fold higher than the linoleic acid concentration found to be present in the alcohol-extracted *Salvia hispanica* seed extract at 100 µg/ml when treating melan-a cells as described in FIG. 2. Further, the 100 µg/ml α-linolenic acid concentration was about 9-fold higher than the α-linolenic acid concentration found to be present in the alcohol-extracted *Salvia hispanica* seed extract at 100 µg/ml in FIG. 2. WST-1 assays showed that linoleic acid and α-linolenic acid were not cytotoxic to melan-a cells at the concentrations tested.

Figure 3:
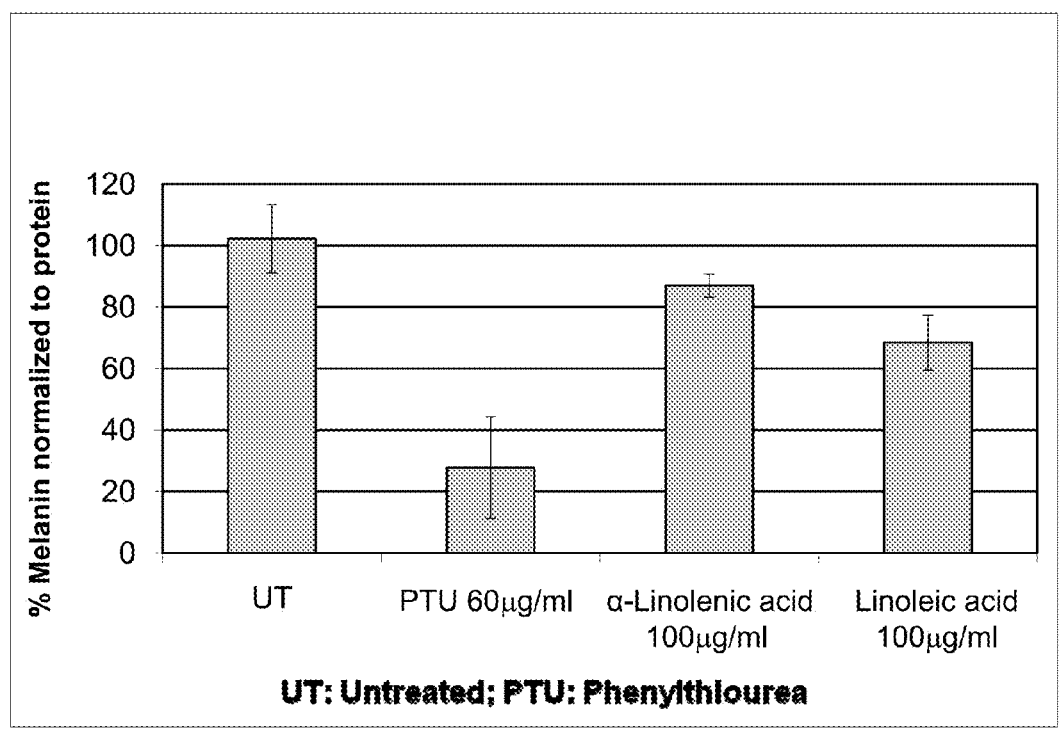
FIG. 3 illustrates the results of a melanin inhibition assay evaluating treatment of melan-a cells with linoleic acid or α-linolenic acid at 100 μg/ml.

As shown in FIG. 3, the higher linoleic acid and α-linolenic acid concentrations achieved comparatively minor reductions in melanin content, whereby the inhibitory activities were not commensurate with those observed in the chia seed alcohol extracts as shown in FIG. 2. These unexpected results suggest that the efficacy of the alcohol extracted chia seed extract in inhibiting melanin content is largely due to undetermined chemical substances distinct from linoleic acid and/or α-linolenic acid.

Example 5

Treatment with Chia Seed and Pomegranate Fruit Extracts

In another melanin inhibition experiment, melan-a cells were treated with an alcohol-extracted *Salvia hispanica* (chia) extract alone at a concentration of 50 µg/ml or as a combination of two extracts, an alcohol-extracted *Salvia hispanica* (chia) extract and a *Punica granatum* (pomegranate) fruit extract having a 20% Punicalagin content, each at 25 µg/ml for a combined extract concentration of 50 µg/ml. As shown in FIG. 4, an alcohol-extracted *Salvia hispanica* seed extract in combination with a *Punica granatum* (pomegranate) extract at a 1:1 ratio in a combined extract concentration of 50 µg/ml showed a significantly enhanced efficacy in reducing total melanin content compared to the alcohol-extracted *Salvia hispanica* seed extract at a concentration of 50 µg/ml. Specifically, the combination of these two extracts reduced melanin content by about 68% compared to about 17% reduction by the alcohol-extracted *Salvia hispanica* seed extract alone. This level of melanin inhibition was nearly equivalent to the 70% reduction in the presence of the phenylthiourea positive control.

Example 6

Exemplary Composition

The following is an example of a formulation according to the present invention.

TABLE 1

| Ingredients | Amount (percent) |
|---|---|
| Isopropyl palmitate | 2.0-8.0 |
| Glycerin | 1.0-5.0 |
| Behenyl alcohol | 1.0-5.0 |
| PEG-100 Stearate | 1.0-5.0 |
| Butylene glycol | 2.5-10.0 |
| Chia seed extract | 0.1-2.0 |
| Pomegranate extract | 0.1-2.0 |
| Sorbitan stearate | 0.2-2.5 |
| Cetyl alcohol | 0.1-2.0 |
| Dimethicone | 0.1-2.0 |
| Fragrance | 0.05-1.0 |
| Xanthan gum | 0.05-1.0 |
| Methylparaben | 0.05-1.0 |
| Chlorphenesin | 0.05-1.0 |
| Water | q.s. to 100.0 |

While the invention has been described in conjunction with specific embodiments, it is to be understood that many alternatives, modifications, and variations will be apparent to those skilled in the art in light of the foregoing description. Accordingly, this invention is intended to embrace all such alternatives, modifications, and variations that fall within the spirit and scope of the appended claims.

The invention claimed is:

1. A topical composition comprising from about 0.2 μg/ml to about 50 μg/ml of a *Salvia hispanica* seed extract in a glycol carrier and from about 0.2 μg/ml to about 50 μg/ml of a *Punica granatum* extract, wherein the *Salvia hispanica* and the *Punica granatum* are present in a ratio of about 1:1 and wherein the *Salvia hispanica* seed extract is obtained from a process that uses only a single extraction step and uses only a single alcoholic solvent.

2. The composition of claim 1, wherein the alcohol is selected from the group consisting of methanol, ethanol, propanol, isopropanol, and butanol.

3. The composition of claim 2, wherein the alcohol is ethanol.

4. The composition of claim 1, wherein the glycol carrier is pentylene glycol.

5. The composition of claim 1, further comprising a permeation enhancer.

6. The composition of claim 5, wherein the glycol carrier comprises pentylene glycol and the permeation enhancer comprises dimethyl sulfoxide.

7. The composition of claim 1, wherein the *Punica granatum* extract contains a punicalagin content between about 10% and 30%.

* * * * *